United States Patent [19]

Taylor

[11] Patent Number: 5,073,640

[45] Date of Patent: Dec. 17, 1991

[54] CYCLICDIHYDROXY COMPOUNDS

[75] Inventor: Stephen C. Taylor, Darlington, United Kingdom

[73] Assignee: Imperial Chemical Industries PLC, London, England

[21] Appl. No.: 420,367

[22] Filed: Oct. 12, 1989

[30] Foreign Application Priority Data

Oct. 13, 1988 [GB] United Kingdom ............... 8823977

[51] Int. Cl.$^5$ ............... C07C 69/25; C07C 69/18; C07C 69/30; C12P 7/62
[52] U.S. Cl. ............... 560/254; 560/231; 260/410.5; 435/135
[58] Field of Search ............... 568/832; 560/231, 254; 435/135

[56] References Cited

U.S. PATENT DOCUMENTS

Re. 33,307  8/1990  Taylor et al. ............ 568/832
4,740,638  4/1988  Taylor et al. ............ 568/833

FOREIGN PATENT DOCUMENTS 0076606  3/1983  European Pat. Off. .
0250122  12/1987  European Pat. Off. .

OTHER PUBLICATIONS

Castrantas et al., "1-History, Education, and Documentation", Chemical Abstracts, vol. 73, No. 1, Jul. 7, 1970.
Gibson et al., *Biochemistry*, vol. 9(7), 1970, pp. 1626–1630.

*Primary Examiner*—Johnnie R. Brown
*Assistant Examiner*—Pamela S. Webber
*Attorney, Agent, or Firm*—Cushman, Darby & Cushman

[57] ABSTRACT

Substituted cis-1,2-dihydroxy-cyclohexa-3,5-diene compounds, useful as intermediates in the production of phenols and catechols for use as intermediates in the production of drugs, herbicides, insecticides and as chiral synthons, in particular benzyl acetate cis glycol. A process for producing the novel compounds is also claimed.

3 Claims, No Drawings

CYCLICDIHYDROXY COMPOUNDS

This invention relates to novel cyclic dihydroxy compounds and to a process for producing them.

Certain cis 1,2-dihydroxycyclohexadienes are useful in the preparation of novel polymers. In our European Patent Specification No. 76606 B we disclose a process for the production of such dihydroxy cyclohexadienes from aromatic compounds using mutant strains of the species *Pseudomonas putida*, in particular mutants of *P. putida* strains NCIB 11767 and NCIB 11680. The enzyme which catalyses the reaction involved in this process is an aromatic dioxygenase which catalyses a reaction between certain aromatic compounds and oxygen for example the reaction below between benzene and oxygen

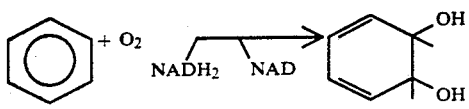

When strains such as *P. putida* NCIB 11767 and NCIB 11680 are fed with aromatics, the dihydroxy cyclohexadiene compounds do not accumulate since they are rapidly further oxidized via catechols to products of intermediary metabolism. However in our European Specification 76606 we describe how mutants of these microorganisms may be produced which are unable to oxidize the dihydroxy cyclohexadienes and these compounds as a result accumulate when such mutants are exposed to aromatic substrates. Some of these mutants must be grown in the presence of benzene or toluene if the activity of the aromatic dioxygenase enzyme needed to convert aromatics to dihydroxy cyclohexadienes is to be induced. Some of the mutants are constitutive for the enzyme which causes production of the dihydroxy cyclohexadienes ("constitutive strains"). These constitutive strains do not require prior enzyme induction by benzene or toluene in order to produce dihydroxy cyclohexadienes.

In our European Patent Specification No. 250122A we disclose an improved method for the production of cells of *Pseudomonas putida* comprising an enzyme capable of converting an aromatic or substituted aromatic compound to a corresponding cyclic dihydroxy compound comprising a 1,2-dihydroxy-cyclohexa-3,5-diene ring which comprises growing cells of a first mutant strain of *Pseudomonas putida* (as hereinafter defined) in a culture medium containing an inducer compound other than benzene or toluene which causes induction of the enzyme capable of converting the aromatic or substituted aromatic compound to the corresponding cyclic dihydroxy compound and which is not itself a substrate for said enzyme.

Alternative processes or the production of cyclic dihydroxy compounds from aromatics which are described in the literature include that described by Gibson D. T. et. al., Biochemistry, 9, 1970, 1626–1630.

The process of our European Patent 76606 B, particularly when carried out using microbial cells produced by the method of European Patent Specification 250122 enables conversions of aromatic compounds to be achieved to produce some interesting new cyclic dihydroxy compounds. In our European Patent Specification No. 253485A we have described a number of such novel compounds. Further compounds are described in the present specification.

According to the present invention we provide compounds having the general formula:

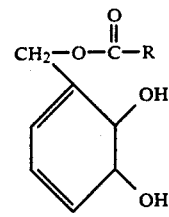

wherein R is an alkyl or substituted alkyl group.

Preferably R is an unsubstituted alkyl group having from 1 to 4 carbon atoms with the compound in which R is methyl being particularly preferred. This particularly preferred compound is hereinafter referred to as benzyl acetate cis glycol.

Further according to the present invention we provide a process for the production of a cyclic dihydroxy compound having the general formula:

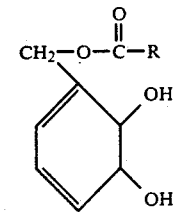

wherein R is an alkyl or substituted alkyl group, which comprises supplying a corresponding substituted aromatic compound, having the general formula:

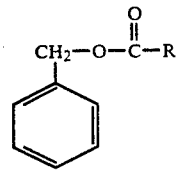

and an energy source to a strain which is a first mutant strain or a constitutive mutant strain of *Pseudomonas putida* (both as hereinafter defined) in a medium which supports little or no growth of cells of the strain.

When the preferred compound of the invention is to be produced by the process of the invention R in the substituted aromatic compound will be —CH$_3$.

The first mutant strain is a strain of *Pseudomonas putida:*
 (a) in which an enzyme can be induced which can convert an aromatic or substituted aromatic compound into a corresponding cyclic dihydroxy compound,
 (b) which is not capable of growing on benzene or toluene, and
 (c) which is derived from a strain of *P. putida* which is capable of growth on benzene or toluene.

The constitutive mutant is produced from the first mutant strain of *P. putida* and is constitutive for an enzyme which converts an aromatic or substituted aromatic compound into a corresponding cyclic dihydroxy compound.

Preferably the first mutant strain is derived from *P. putida* strain NCIB 11680 or NCIB 11767 deposited at the National Collections of Industrial and Marine Bacteria (NCIMB), PO Box 31, 135 Abbey Road, Aberdeen, AB9 8DG, Scotland, UK.

Examples of suitable energy sources for the process of the invention include, alcohols such as ethanol, carboxylic acids such as acetic acid and carbohydrates such as glucose. Preferred energy sources are ethanol and acetic acid.

Strains which are very suitable as first mutant strains in the method or the process of the invention, may be prepared by treating *Pseudomonas putida* NCIB 11680 or preferably *Pseudomonas putida* NCIB 11767 under mutating conditions therefore to give mutant strains which are no longer capable of utilizing toluene or benzene as a sole source of carbon for growth and which when grown, in a liquid medium containing pyruvic acid as a carbon source, in the presence of toluene, excrete a substance which has a UV absorbance peak at 265 nm. This mutation may be effected by chemical and/or physical means. Chemical mutation may be effected for example by treatment of the microorganism with N-methyl-N'-nitrosoguanidine, e.g. as described by Ornston, Journal of Biological Chemistry, 1966, Volume 241, pages 3800-3810. Physical mutation may be effected by electromagnetic radiation, e.g. UV light.

The constitutive mutant strain for use in the process of the invention is suitably prepared by treating the first mutant strain of *Pseudomonas putida* NCIB 11767 under mutating conditions as hereinbefore described to give strains which after growth in the absence of an aromatic compound, have the ability to produce cyclic dihydroxy compounds from aromatic compounds. Choice of suitable constitutive strains from the product of the mutation treatment may be facilitated by growing the cells after mutation on a solid agar medium containing pyruvic acid or glucose as carbon source. After growth, the colonies on the agar plates may be sprayed with a solution of catechol in water, colonies of cells which rapidly turn yellow/green are constitutive for an enzyme which converts catechol into 2-hydroxymuconic semialdehyde (Nozaki, Topics in Current Chemistry (English Review) 1979, Volume 78, pages 145-186). This enzyme catalyses one of the steps in the oxidative degradation of benzene in *Pseudomonas putida* NCIB 11680 and *Pseudomonas putida* NCIB 11767 and we have found that it is linked in its expression to the enzyme which converts benzene to the cyclic dihydroxy compound. Therefore those cells which turn green on exposure to catechol are the desired constitutive strain.

The constitutive mutant strain may be susceptible to catabolite repression by carbon sources such as glucose and casamino acids. Improved constitutive strains which are not susceptible to such catabolite repression may be obtained by further mutation of the constitutive strains, by treatments as hereinbefore described. The improved constitutive strains can be detected by growing colonies of the constitutive strains which have been subjected to a mutation treatment on an agar medium which contains a mixture of glucose and casamino acids as carbon sources, the colonies which turn yellow/green on exposure to catechol comprise the improved constitutive strain.

When the first mutant is produced by the method of European Patent Specification 250122, cells of the mutant strain may be grown in conventional growth media (modified to include an inducer compound) as a continuous, batch or fed-batch technique.

The growth medium in which first mutant strains for use in the process of the invention may be grown comprises an aqueous mineral salts solution and a suitable carbon source. The carbon source may be, for example, acetic acid, glucose or ethanol. The concentration of carbon source can vary over a wide range but is generally between 1% (w/w) and 20% (w/w). Oxygen or an oxygen containing gas, must be present during the growth period. The temperature of the medium during the growth period may vary considerably but normally will be in the range of 25° C. to 35° C. The pH of the medium is kept within the range of 5.5 to 8.0 during growth and preferably at 6.5 to 7.5. The size of the culture can vary considerably for example between 1.5 and 500 liters.

Following the growth period the cells are used in the process of the invention. The cells may be harvested, for example by centrifugation or flocculation, or they may be used directly in the process of the invention. Where the cells are harvested they are resuspended in a mineral salts solution which does not support significant cell growth, e.g. phosphate or buffer solutions or a growth medium which is conventional but lacks or contains little of one or more essential elements. Typically the concentration of resuspended cells is 1 to 30 grams dry weight per liter. The cells are kept at a temperature of 20° C. to 40° C. and the pH maintained between 6.5 and 8.5. Oxygen or an oxygen containing gas is added to the cell suspension such that the oxygen tension is kept at greater than 1% of saturation. A suitable energy source is supplied, to the cell suspension such that the concentration of the energy source is maintained at a suitable concentration, preferably between 0.05% (w/w) and 0.5% (w/w).

The substituted aromatic compound may be added to the cell suspension as a vapour in the stream of oxygen or oxygen-containing gas but preferably, when it is liquid, it is added as a liquid.

The rate of addition of the substituted aromatic compound to the culture of the mutant strain in the process of the invention is typically about 0.5 to 10 grams per gram dry weight of cells per hour. The rate of addition of the energy source may vary during the conversion but is typically in the range 0.1 to 2.0 grams per gram dry weight of cells per hour. The productive lifetime of the cell suspension is typically between 5 and 50 hours. After this period the cells are removed by centrifugation and/or flocculation. Fresh cells may be added to the supernatant liquor and the process repeated. At the end of the process the supernatant liquor typically contains between 10 and 50 grams per liter of a compound of the invention.

The new cyclic dihydroxy compounds produced by the process of the invention are preferably extracted from the aqueous reaction mixture by solvent extraction with a suitable polar solvent. Examples of polar solvents which may be used include inter alia ethyl acetate, diethyl ether and methylene chloride. More preferably continuous extraction procedures are employed. However, we do not exclude the possibility that, for example, the aqueous medium, after separation of the cells, is evaporated and the residue dissolved in a suitable solvent, e.g. methanol, ethanol or methylene chloride.

The dihydroxy compounds prepared by the process of the invention may be converted into derivatives thereof, e.g. acetate, benzoate, pivalate, carbonate, which derivatives may be converted into polymers and copolymers thereof.

The new compounds of the invention can be used as starting materials for the synthesis of natural product analogues, for example inositols (c.f. Ley, S. V. and Sternfield, F., Tetrahedron Letters, 1988 in press). The new compounds now allow for a much broader range of chemical options and syntheses than was previously available giving rise to novel natural product analogues.

GROWTH MEDIA USED IN PREPARATION OF MUTANTS AND IN EXAMPLES

1. Bauschop and Elsdon's medium as described in Journal of General Microbiology, 1960, Volume 23, pages 457–469.
2. Luria liquid medium as described in "Experiments in Molecular Genetics" by J H Miller, published by Cold Spring Harbor Laboratories, New York, 1972.

PREPARATION OF MUTANT STRAINS OF PSEUDOMONAS PUTIDA NCIB 11767 FOR USE IN THE PRESENT INVENTION

*Pseudomonas putida* NCIB 11767 was grown to early exponential phase in Luria liquid medium. The cells were harvested by centrifugation and resuspended at a concentration of 0.2 grams dry cell weight per liter in 20 ml of 25 millimolar citric acid-sodium citrate buffer, pH 5.5 containing 1 mg of N-methyl-N'-nitro-N-nitroso-guanidine (NTG). After 45 minutes at 30° C. the cells were harvested by centrifugation, washed twice with Bauschop and Elsdon's medium and then grown overnight in this medium when containing 0.3% (w/v) sodium pyruvate at 30° C. After serial dilution, cells were plated on a Bauschop and Elsdon's medium agar containing 0.3 millimolar sodium pyruvate and incubated in 1 liter paint tins each containing 0.5 ml benzene in a vial. After 3 days at 30° C.; 144 prospective mutants, i.e. colonies less than 0.5 mm diameter, were picked off and regrown on a 0.2% w/v sodium pyruvate, Bauschop and Elsdon's medium agar.

90 of these mutants were screened in liquid culture for the production from benzene of a compound absorbing at 260 nm. One mutant which gave a supernatant liquid with a maximum absorbance at 260 nanometers of 37 is hereinafter referred to for convenience as mutant strain B.

PREPARATION OF CONSTITUTIVE STRAINS FROM MUTANT B

The procedure used for mutagenisis was as hereinbefore described. After treatment with NTG, the washed, diluted cells were plated onto Bauschop and Eldson's medium agar plus 10 millimolar sodium pyruvate. After two days at 30° C., colonies were sprayed with a solution of catechol in water (0.5 molar) and those whcih turned yellow/green after 5 minutes were selected. From a total of $1.8 \times 10^5$ colonies screened, 35 yellow/green colonies were selected. Each of these was grown overnight in 16 ml of Bauschop and Elsdon's medium plus 0.3% (w/v) sodium pyruvate. Cells were harvested and resuspended in 10 ml of 25 mM potassium phosphate buffer, pH 7.8, containing 0.4% (v/v) ethanol. These cultures, in 250 ml conical flasks, were incubated overnight, each in the presence of 0.5 ml toluene. Supernatants were examined after this time for compounds absorbing at 265 nm. A constitutive mutant which gave an absorbance at 265 nm of 250 was selected and is hereinafter referred to for convenience as mutant strain C.

Mutant strain C was grown at 30° C. in 20 ml of Luria liquid medium to early exponential phase and after harvesting, cells were resuspended in 40 ml of 0.1 molar $MgSO_4.7H_2O$. A 5 ml aliquot was UV-irradiated in a glass petri dish for 45 seconds at a dose of 1.6 $uw/cm^2 \times 100$. The cells were then grown in the dark in five 20 ml aliquots of Bauschop and Elsdon's medium plus 10 millimolar sodium pyruvate.

After 2 days at 30° C. cultures were serially diluted and plated onto Bauschop and Elsdon's medium plus 75 millimolar glucose and 1% (w/v) vitamin free casamino acids (ex Difco Ind., Detroit, Mich., USA) and incubated for a further 2 days at 30° C. Colonies were then sprayed with catechol as hereinbefore described and yellow/green colonies were selected. From a total of $4 \times 10^4$ colonies screened, 10 were selected and grown overnight in 10 ml of Bauschop and Elsdon's medium plus 75 millimolar glucose and 1% (w/v) casamino acids at 30° C. Cells were harvested and resuspended as above in phosphate buffer plus ethanol and irradiated at 70° C. in the presence of 0.5 ml toluene as hereinbefore described. A constitutive mutant, less affected then mutant C by catabolite repression was selected which gave an absorbance at 265 nm of 61.2. (Mutant strain C under identical conditions produced an absorbance of 15.6). This mutant is hereinafter referred to for convenience as mutant strain D. The invention is illustrated by the following Example:

EXAMPLE

Production of cis-3-(hydroxymethyl) 3,5-cyclohexadine-1,2-diola acetate ether (benzyl acetate cis glycol) by the process of the invention.

Mutant D was gronw overnight at 30° C. with shaking in 200 ml of Bauschop and Elsdon's medium containing 1% w/v sodium pyruvate. The 200 ml culture was then used to inoculate 10 liters of a medium containing concentrated phosphoric acid (2.2 g.$l^{-1}$), $mgSO_4$ $7H_2O$ (0.8 g.$l^{-1}$), $K_2SO_4$ (0.45 g.$l^{-1}$), $(NH_4)_2SO_4$ (5 g.$l^{-1}$), $FeSO_4$ $7H_2O$ (0.04 g.$l^{-1}$), $CuSO_4$ $5H_2O$ (1 mg.$l^{-1}$), $MnSO_4$ $4H_2O$ (5 mg.$l^{-1}$), $CaCO_3$ (65 mg.$l^{-1}$) adjusted to pH 6.8 with 4M sodium hydroxide. This was stirred at 500 rpm, maintained at 28° C. and ¼vvm. air was added. Glucose was added from a 40% w/v concentrated solution at a rate of 1 g.$l^{-1}$.$h^{-1}$ and the pH was maintained at 6.8 by automatic titration with 4M NaOH. All solutions were sterilised by autoclaving at 121° C. for 1 hour prior to use.

After 16 hours the cell density in the fermenter was 5 g.$l^{-1}$. Cells of mutant D were harvested by centrifugation.

In a fermenter the cells were resuspended in 4 liters of phosphate buffer ($KH_2PO_4$ 66 g$l^{-1}$[10 mls $l^{-1}$] and $K_2HPO_4$ 66 g$l^{-1}$ [20 mls $l^{-1}$]) and the pH adjusted to 7.3. Temperature was maintained at 27.5° C. The absorbance at 600 nm of the cell suspension was between 12–20 units, corresponding to approximately 5 g. cell dry weight per liter. Stirring of the broth was done at 500 rpm. Ethanol was added to a concentration of 0.5% v/v. Benzyl acetate was added to the broth from a syringe pump at a steady rate of 6 ml.$h^{-1}$. The concentration of ethanol in the broth was monitored by gas chromatography and 5 ml aliquots of ethanol were added when the concentration fell below 2 g$l^{-1}$. The formation of benzyl acetate cis-glycol was monitored by measuring the absorbance of the broth supernatant at 375 nm. When the absorbance at 375 nm ceased rising the broth was taken to pH 10 and the cells were removed by centrifugation at 5000 g. The supernatant was evaporated under reduced pressure at 60° C. to 200-250 ml and the concentrate continuously extracted overnight with two liters of dichloromethane. The dichloromethane was concentrated by evaporation to yield an oil. To this oil was added 10 ml of isopropyl ether. The isopropyl ether was decanted and chilled to −78° C. when a crop of fine crystals of benzyl acetate-cis-glycol were formed.

The measured molar extinction coefficient of this product at 375 nm was 7400 representing a concentration of benzyl acetate cis glycol in the broth of 9.3 g.l$^{-1}$.

I claim:
1. A compound having the formula:

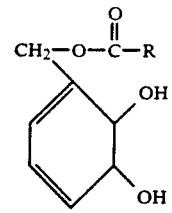

wherein R is selected from the class consisting of alkyl groups.

2. A compound according to claim 1 wherein R is an unsubstituted alkyl group having from 1 to 4 carbon atoms.

3. A compound according to claim 2 wherein R is a methyl group.

* * * * *